United States Patent [19]

Di Gioacchino et al.

[11] Patent Number: 5,026,906

[45] Date of Patent: Jun. 25, 1991

[54] METHOD OF PREPARATION OF OPTICALLY ACTIVE ALPHA-AMINO-ACIDS

[75] Inventors: Sandro Di Gioacchino; Antonio Paolinelli; Luciano Re, all of Rome, Italy

[73] Assignee: Eniricerche S.p.A., Milan, Italy

[21] Appl. No.: 486,307

[22] Filed: Feb. 28, 1990

Related U.S. Application Data

[62] Division of Ser. No. 181,673, Apr. 14, 1988, Pat. No. 4,925,978.

[30] Foreign Application Priority Data

Apr. 28, 1987 [IT]  Italy .................................. 20291 A/87

[51] Int. Cl.$^5$ ............................................ C07C 227/00
[52] U.S. Cl. .................................... 562/437; 562/507; 562/560
[58] Field of Search ......................... 562/437, 507, 560

[56] References Cited

PUBLICATIONS

Lutsenko et al., Chem. Abst., vol. 94, #46,742h (1981).
Challis et al., Chem. Abst., vol. 91, #91276h (1974).
Ohashi et al., Chem. Abst., vol. 90, #39270w (1979).

Primary Examiner—James H. Reamer
Attorney, Agent, or Firm—Oblon, Spivak, McClelland, Maier & Neustadt

[57] ABSTRACT

A new process of synthesis of optically active α-amino acids is described through nitrosation in a non-aqueous, aprotic system of the corresponding N-carbamyl derivatives followed by decomposition of the thus obtained N-nitroso derivatives in aqueous acidic medium. The process, which is of a general applicability, leads to a remarkable increase in the reaction yields, due to the suppression of the main side reaction leading to the corresponding α-hydroxy-acid. Some N-nitroso intermediates, which can be recovered from the process of the invention, are also described.

2 Claims, No Drawings

METHOD OF PREPARATION OF OPTICALLY ACTIVE ALPHA-AMINO-ACIDS

This is a division of application Ser. No. 07/181,673, filed on Apr. 14, 1988, now U.S. Pat. No. 4,925,978.

The present invention refers to a new process for the preparation of optically active α-amino-acids. More particularly, a first object of the present invention is a process of preparation of an α-amino-acid of general formula (I)

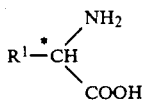

wherein
the asterisk denotes an asymmetric carbon atom having a particular stereochemical configuration, and
$R^1$ represents an optionally substituted alkyl, cycloalkyl, cycloalkenyl, aryl, or arylalkyl group, via nitrosation of the corresponding N-carbamyl derivative of general formula (II)

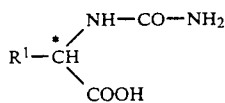

wherein
$R^1$ is as defined above and the asterisk means that the absolute configuration of the starred carbon atom in the N-carbamyl derivative (II) is the same as that of the corresponding carbon atom in the desired α-amino-acid (I), with nitrogen oxides in a non-aqueous, aprotic system, followed by decomposition of the thus obtained intermediate, in aqueous acidic conditions.

For the purposes of the present invention, the term "optionally substituted alkyl radical" designates a straight or branched alkyl radical containing from 1 to to 10 carbon atoms, e.g. methyl, ethyl, isopropyl, isobutyl, sec-butyl, hexyl, isooctyl, etc., which may bear one or more substituents independently selected from the group consisting of —COOH, —COOR$^2$, —YCOR$^2$, —YSO$_2$R$^2$, —YR$^2$, —SSR$^2$, and halogen, wherein R$^2$ represents an alkyl, arylalkyl, or aryl radical of from 1 to 20 carbon atoms, and Y is S or O; the term "optionally substituted cycloalkyl or cycloalkenyl radical" identifies a cycloalkyl or cycloalkenyl radical containing from 5 to 10 carbon atoms and optionally one or two double bonds, e.g. cyclopentyl, cyclohexyl, cycloheptyl, cyclooctyl, 2-methyl-cyclohexyl, 1,4-cyclohexadienyl, 1,4-cyclooctadienyl, etc., which may be unsubstituted or bear one or more substituents independently selected from the above defined group; the term "optionally substituted aryl radical" designates a phenyl radical which may optionally bear one or more substituents independently selected from the group consisting of alkyl, —OH, —COOH, —COOR$^2$, —YCOR$^2$, —YSO$_2$R$^2$, —YR$^2$, —SSR$^2$, halogen, nitro, and halo-alkyl, wherein R$^2$ and Y are as defined above; finally, the term "optionally substituted arylalkyl radical" designates a substituted or unsubstituted alkyl radical, as above defined, bearing one or more "aryl" groups as above defined.

The optically active α-amino-acids of formula (I) are of particular interest as chemical intermediates; more particularly, some α-amino-acids of formula (I) wherein the α-carbon atom is of the D-configuration are key intermediates in the preparation of β-lactam antibiotics (mainly semi-synthetic penicillins and cephalosporins), peptide hormones, pyrethroids, etc..

As an example, D-(—)-(4-hydroxyphenyl)-glycine and D-(—)-phenylglycine are key intermediates in the industrial synthesis of amoxycillin and ampicillin respectively; while D-(—)-2-amino-2-(1,4-cylcohexadien-1-yl)acetic acid may conveniently be employed in the acylation of 7-amino-cephalosporanic acid to give cefradin.

In view of the industrial interest of the end products, a preferred embodiment of the present invention is the process for preparing an α-amino-acid of formula (I) wherein $R^1$ represents an optionally substituted alkyl or phenyl radical.

A most preferred embodiment is the process for preparing an α-amino-acid of formula (I) wherein $R^1$ represents an optionally substituted alkyl or phenyl radical, and the starred carbon atom is of the D-configuration.

Among the different methods of synthesis of these optically active α-amino-acids, conversion of the corresponding N-carbamyl derivatives, has recently been developed, as it has been found that these last compounds can be prepared conveniently in optically active form, by stereoselective enzymatic hydrolysis of the corresponding 5-substituted-D,L-hydantoins of formula (V)

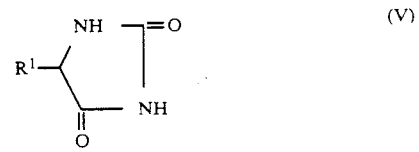

(see for instance S. Takahashi in "Progress in Industrial Microbiology", Vol. 24, pp.269–279, Elsevier, Amsterdam, (1986), and DE-OS 2,621,076). The prior art methods for converting the N-carbamyl derivatives of formula (II) into the corresponding α-amino-acids (I), involve nitrosation of compounds (II) under conventional nitrosation conditions, thus employing an alkaline nitrite, e.g. sodium or potassium nitrite, in aqueous medium, in the presence of a strong mineral acid, such as hydrochloric acid or sulphuric acid. Under these reaction conditions, the nitrosated intermediate is converted in situ in α-amino-acid (I), which in its turn, in the presence of the nitrosating agent, is susceptible to be further nitrosated and converted into the corresponding α-hydroxy-acid (VI)

Several improvements in the N-carbamyl derivative (II)/α-amino-acid (I) conversion process, via nitrosation, have been set up in the last 10 years. The most important ones are those described in DE-OS 2,615,594 and Japanese kokai 78 103,441. According to the method described in DE-OS 2,615,594, the reaction is carried out in the presence of an acidic resin which is aimed at blocking the obtained α-amino-acid (I), thus avoiding its nitrosation and conversion to α-hydroxyacid. However, in order to get high yields in α-amino-acid (I) by this method, it is necessary to use a very high resin/substrate ratio and this makes the process expensive and of difficult industrial application. According to Japanese kokai 78 103,441, particular reaction conditions must be used in the nitrosation/hydrolysis reaction, i.e. temperature lower than 20° C., and mixtures of water and acetic acid as the reaction media. Also in this case, however, particularly when $R^1$ is phenyl or 4-hydroxy-phenyl, a rather high percentage of α-hydroxy-acid (VI) is obtained as a reaction side-product.

It has now been found and represents a first object of the present invention, that it is possible to nitrosate an N-carbamyl derivative (II) in quantitative yields, using, as the nitrosating agent, a nitrogen oxide such as dinitrogen trioxide or dinitrogen tetraoxide, or a mixture of these oxides in any proportion, and carrying out the reaction in a non-aqueous, aprotic system. The product which is thus obtained consists of a mixture, in varying proportions, of N-nitroso compounds of formula (III) and (IV)

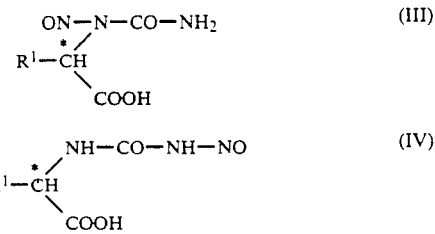

The molar ratio between these N-nitroso intermediates substantially depends on the nitrosation temperature, the composition of the nitrosating mixture and the hydrogen ion activity in the reaction medium.

In particular, it has been observed that the amount of N-nitroso derivative (IV) increases with the nitrosation temperature and with the ionic strenght. It has also been found that it is possible to convert the N-nitroso derivative (III) which possibly forms, into the isomer (IV), which is the immediate precursor of the desired α-amino-acid, by acid-catalysed rearrangement in strictly controlled conditions.

The mixture of N-nitroso derivatives (III) and (IV) obtained in the nitrosation of the corresponding N-carbamyl derivative according to the process of the present invention, as well as the N-nitroso derivatives of formula (IV) in a substantially pure form, represent therefore a second object of the present invention.

Both intermediates, finally, can be easily converted into the corresponding α-amino-acids (I) in aqueous acidic medium, with very high yield and optical purity as the intermediate (III) undergoes an acid-catalysed rearrangement in situ to the intermediate (IV) which is the direct precursor of the α-amino-acid.

The two-step process of the present invention, which avoids formation of the undesired α-hydroxy-acid, affords a remarkable increase of the overall yields in α-amino-acid.

The nitrosation reaction according to the process of the present invention is conveniently conducted in the presence of an aprotic, preferably polar, anhydrous organic solvent which does not negatively interfere with the reaction course.

Suitable organic solvents are, for instance, linear or cyclic ethers, such as methyl isopropyl ether, tetrahydrofuran, and dioxane, aliphatic halogenated hydrocarbons, such as methylene chloride, chloroform, dichloroethane, etc., optionally substituted aromatic hydrocarbons, such as benzene, toluene, benzonitrile, and nitrobenzene, and other commonly used solvents such as dimethylformamide, dimethylsulfoxide, acetonitrile, etc..

Preferred solvents are however cyclic ethers and aliphatic halogenated hydrocarbons.

The reaction is generally carried out at a temperature comprised between $-20°$ C. and $+50°$ C.

It is however possible to use temperatures higher than 50° C., controlling that the intermediate does not decompose spontaneously, or lower than $-20°$ C., thus prolonging the reaction time.

Preferably, however, the nitrosation step is carried out at a temperature comprised between 0° C. and room temperature.

The nitrogen oxides which are used in this first step, can be employed as single compounds or, more conveniently, as mixtures thereof. In this case, the mixture can be easily obtained in situ, by bubbling a mixture of air and nitrogen monooxide directly into the reaction vessel, or, it may be prepared in a separate vessel, by reacting an alkaline nitrite with a mineral acid, e.g. sulphuric or hydrochloric acid, and streamed into the nitrosation reaction vessel by an inert gas, e.g. nitrogen.

Nitrosation is conveniently carried out at atmospheric pressure. Higher pressures, up to one hundred atmospheres, may however be employed in this step. At the end of the nitrosation reaction, which can be easily monitored by checking the disappearance of the starting N-carbamyl derivatives by means of chromatographic techniques, the nitrosated product is recovered by conventional techniques, i.e. by evaporating off the organic solvent, preferably under reduced pressure.

The mixture of the two nitroso derivatives of formula (III) and (IV) which is thus obtained, can then be converted into the desired α-amino-acid (I) through decomposition in aqueous acidic medium. In the actual practice, the decomposition reaction is carried out in water or in a mixture of water and an organic solvent miscible with water, at a pH adjusted to $<4$, and preferably $<2$, by the addition of a strong, mineral or organic, acid. Suitable acids are for instance hydrochloric acid, sulphuric acid, sulphonic organic acids, e.g. methanesulphonic acid, p-toluenesulphonic acid, and the organic halogenated carboxylic acids, e.g. trifluoro- and trichloro-acetic acid. Organic solvents miscible with water which can suitably be employed in this step are for instance tetrahydrofuran, dioxane, acetone, dimethylformamide, aliphatic alcohols, etc. According to a preferred embodiment of the invention, this step is carried out in water or in a mixture of water and organic solvent miscible with water with a boiling point lower than that of water, using a mineral acid as the acidifying agent. This allows an easier recovery of the end α-amino-acid.

The decomposition reaction can be carried out at a temperature generally comprised between $+5°$ C. and the reflux temperature of the reaction mixture. Preferably, however, a temperature comprised between 10 and 100° C. is employed, and more preferably a temperature near to room temperature.

The reaction, whose completion can be easily ascertained by checking gas ($N_2$ and $CO_2$) evolution, is typically complete in a few hours.

The desired α-amino-acid is then recovered by precipitating it from the aqueous solution, with or without prior removal of the organic solvent by evaporation, adjusting the pH of the solution to the isoelectric point.

As basic agents in this precipitation there can be used the alkaline or alkaline earth metal carbonates and hydroxides, e.g. sodium hydroxide, sodium carbonate, and potassium bicarbonate, and ammonium hydroxide.

The thus obtained products are generally characterized by an optical purity sufficient to allow their use in the subsequent syntheses. If, however, a greater purity is desired, the product can be easily purified according to the conventional techniques, for instance, by crystallization from water, i.e. dissolving it in slightly acidic water and then bringing the pH to the isoelectric point, or from water/alcohol, typically water/ethanol.

If, on the contrary, recovery of the intermediate N-nitroso derivative (IV), in a substantially pure form, is desired, the mixture of the two N-nitroso derivatives, which is obtained in the nitrosation step, is submitted to an acid-catalysed rearrangement, in very mild conditions. In particular, this conversion is carried out at a temperature near to or lower than room temperature, in a reaction medium consisting of water optionally mixed with a suitable organic solvent, brought to pH <4, by the addition of an inorganic or organic acid. When the rearrangement, which should be monitored carefully by chromatography, is over, neutralization with a base, followed by extraction of the aqueous solution with an organic solvent immiscible with water and evaporation thereof, leads to the intermediate N-nitroso compound of formula (IV) in a substantially pure form.

The following examples, which describe in detail the process of the present invention in some representative, preferred embodiments thereof, are to be employed for a better understanding of the invention but should not be interpreted as a limitation to the scopes thereof.

EXAMPLE 1

N-carbamyl-N-nitroso-D-valine (III: $R^1$=i-Pr) and N-(N'-nitrosocarbamyl)-D-valine (IV: $R^1$=i-Pr)

A mixture of $N_2O_3$ and $N_2O_4$, obtained in situ by mixing NO with air (feeding NO/air ratio, by volume,=2.5), is bubbled at room temperature and atmospheric pressure into a solution of N-carbamyl-D-valine (II: $R^1$=i-Pr; 4.16 g, 26 mmol) in dioxane (60 ml).

The reaction course is monitored by reverse-phase HPLC, eluting with a mixture of a slightly acidic aqueous solution ($H_2SO_4$, 0.04%, w/v), and acetonitrile 9:1, and using an U.V. detector at 220 nm.

After 180 minutes the starting compound has disappeared almost completely and two new reaction products, in a 4/1 ratio, have formed. The solvent is then evaporated off under reduced pressure yielding an oily residue, consisting of a mixture of the N-nitroso derivatives (III) and (IV) (R1 i-Pr), which on standing solidifies in a crystalline uncolored mass.

Yield: 4.8 g (98%).

I.R. (KBr): 3414 ($NH_2$), 3252 (NH), 3191 (NH), 1740 (NCON), 1710 (NCON) $cm^{-1}$.

$^1$H-NMR (DMSO-$d_6$; (Me)$_4$Si δ=0) :0.9 (γ-$CH_3$), 2.1 (β-CH), 2.2 (β-CH), 4.3 (α-CH), 5.1 (α-CH), 8.2 ($NH_2$), 9.07 (NH).

EXAMPLE 2

N-(N'-nitrosocarbamyl)-D-valine (IV: $R^1$=i-Pr)

A portion of the mixture obtained in example 1 (2.0 g, 10 mmol) is reacted, at 20° C., for about 60 minutes, with a 4.5% (w/v) HCl aqueous solution (20 ml). The reaction mixture is then neutralized by the addition of a diluted $NH_4OH$ solution, and extracted with ethyl ether. The organic solvent is then evaporated off yielding the compound of the title as a pure product.

I.R. (KBr): 3190 (NH), 1710 (NCON), 1510, 1410 $cm^{-1}$.

$^1$H-NMR (DMSO-$d_6$; (Me)$_4$Si, δ=0): 0.85 (d, 3H, $γ_1$-$CH_3$), 0.95 (d, 3H, $γ_2$-$CH_3$), 2.1 (m, 1H, β-CH), 4.3 (t, 1H, α-CH), 8.05 (s, 1H, NH), 9.07 (d, 1H, NH); MS: m/e=160, 144, 116, 101.

EXAMPLE 3

D-valine (I: $R^1$=i-Pr)

A suspension of the mixture of example 1 (4.6 g, 24.3 mmol) in a 4.5% (w/v) HCl aqueous solution (30 ml) is stirred at 70° C. for about 12 hours. The resulting solution is cooled to room temperature and slowly brought to pH 6.6 by the addition of a diluted $NH_4OH$ aqueous solution. By under vacuum evaporation, the mixture is brought to a small volume (10 ml) and the precipitate is recovered by filtration. The recovered solid is washed with water and dried under vacuum. D-Valine (1.77 g) with 95.5 % optical purity is thus obtained.

$[α]_D^{20}$=−25.9° (c=2, 5N HCl)(Lit.: $[α]_D^{20}$=−27.5° (c=2, 5N HCl), J.P. Greenstein, J.Biol.Chem., 194, 455, (1952));

M.p.>300° C. (Lit.: 315° C, E.Fischer, Berichte, 39, 2325, (1906));

I.R. identical to that of an authentic sample (Merck). Analysis of the mother liquors from the precipitation of the amino-acid, showed the presence of additional 0.7 g of the desired product, totalling an overall yield, calculated on the starting N-carbamyl derivative (II: $R^1$=i-Pr) of 78.4%.

EXAMPLE 4

N-carbamyl-N-nitroso-D-phenylglycine (III: $R^1$=$C_6H_5$—) and
N-(N'-nitrosocarbamyl)-D-phenylglycine (IV: $R^1$=$C_6H_5$—)

A mixture of nitrogen monooxide/air (2/2.5, v/v) is bubbled, with a flow rate of 12 ml/min, into a stirred suspension of N-carbamyl-D-phenylglycine (II: $R^1$=$C_6H_5$—) (5.0 g, 26 mmol) in anhydrous dioxane (50 ml) at 20° C.

During the reaction the nitroso gases are rapidly adsorbed and the product gradually dissolves in the reaction medium. The reaction course is followed as described in example 1. After 85 minutes, the starting compound has completely disappeared and a mixture of the two nitroso derivatives (III and IV: $R^1$=$C_6H_5$—) has formed. The solvent is then removed by evaporation under reduced pressure yielding a solid residue (5.8 g, 100 % yield).

I.R. (KBr): 1750 (NCON), 1730 (NCON) $cm^{-1}$.

EXAMPLE 5

D-phenylglycine (I: $R^1$=$C_6H_5$—)

The mixture of nitroso derivatives obtained in the foregoing example (5.8 g, 26 mmol) is suspended in a 4.5 % (w/v) HCl aqueous solution (50 ml) and kept under stirring at room temperature. After about 50 minutes gas evolution subsides and HPLC analysis of the reaction mixture shows the complete conversion to D- phenylglycine and the complete absence of mandelic acid (VI: $R^1=C_6H_5—$).

The amino-acid is then precipitated from the reaction medium by shifting the pH to the isoelectric point (pH 6.0) by the addition of NH$_4$OH. The precipitate is recovered by filtration, washed with water and dried under vacuum (1 mmHg, 35° C.) up to constant weight. The compound of the title (2.8 g) is thus obtained, with 97.5 % optical purity.

$[\alpha]_D^{20}=-152°$ (c=1, 1N HCl)(Lit.: $[\alpha]_D^{20}=-156°$ (c=1, 1N HCl), S. Takahashi, J. Ferment. Technol., 57, 328, (1979));

M.p.=300° C. (Lit.: 302=C., E. Fischer, Berichte, 41, 1290, (1908));

I.R. identical to that of an authentic sample (Merck). Analysis of the mother liquors from the precipitation of the amino-acid, showed the presence of additional 0.5 g of D-phenylglycine, affording an overall yield, calculated on the starting N-carbamyl derivative (II: $R^1=C_6H_5—$), of 85 %.

EXAMPLE 6

N-carbamyl-N-nitroso-D-(4-hydroxyphenyl)glycine (III: $R^1=4—HO—C_6H_4—$) and N-(N'-nitrosocarbamyl)-D-(4-hydroxyphenyl)glycine (IV: $R^1=4—HO—C_6H_4—$)

N$_2$O$_3$ (4.0 g) is bubbled within 240 minutes into a stirred solution of N-carbamyl-D-(4-hydroxyphenyl)glycine (II: $R^1=p—HO—C_6H_4—$) (2.7 g, 12.8 mmol) in anhydrous dioxane (40 ml) kept at 15° C. Stirring is continued, at room temperature, overnight. HPLC analysis of the reaction solution showed the formation of two main reaction products. The solvent is evaporated off under reduced pressure yielding a residue (3.0 g, 97.6 % yield) containing the two nitroso compounds of the title.

I.R. (KBr): 1787, 1745, 1723 cm$^{-1}$.

EXAMPLE 7

D-(4-hydroxyphenyl)glycine (I: $R^1=4$-HO—$C_6H_4—$)

The mixture of nitroso derivatives obtained in the foregoing example undergoes decomposition according to the procedure described in example 3, yielding the compound of the title with 95 % optical purity.

COMPARATIVE EXAMPLE

D-phenylglycine (I: $R^1=C_6H_5—$)

The compound of the title is prepared, for comparison purposes, starting from the corresponding N-carbamyl derivative (II: $R^1=C_6H_5—$) by following the method described in Japanese kokai 78 103,441. In particular, a stirred suspension of N-carbamyl-phenylglycine (II: $R^1=C_6H_5—$) (5.0 g, 26.0 mmol) in a H$_2$O/AcOH 1/1 (v/v) mixture (250 ml) containing 25 g of conc.HCl, kept at 20° C., is added within 30 minutes to a solution of NaNO$_2$ (1.98 g, 28.6 mmol) in H$_2$0 (10 ml). After stirring for additional 5 hours at 20° C., HPLC analysis of the reaction mixture shows a 94 % conversion of the starting N-carbamyl derivative with an overall yield in D-phenylglycine of 63 % and an overall yield in D-mandelic acid of 18 %

The solution is brought to a small volume (50 ml) and neutralized with a diluted NH$_4$OH solution adjusting the pH to 6.6. The precipitate is recovered by filtration, washed with H$_2$O and dried under vacuum (1 mmHg) at 35° C., yielding D-phenylglycine (1.89 g, 48 %). Analysis of the mother liquors gives additional 0.6 g of the product.

We claim:

1. A process for preparing a mixture of N-nitroso derivatives of formulas (III) and (IV)

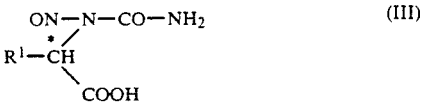

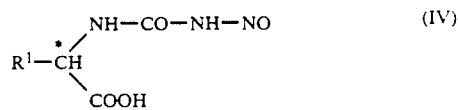

wherein
the asterisk denotes an asymmetric carbon atom having a particular stereochemical configuration, and
$R^1$ represents an optionally substituted alkyl, cycloalkyl, cycloalkenyl, aryl, or arylalkyl group,
which comprises nitrosating the corresponding N-carbamyl derivative of general formula (II)

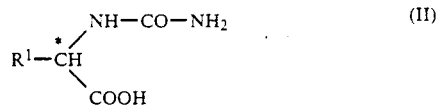

wherein
$R^1$ is as defined above and the asterisk indicates that the absolute configuration of the starred carbon atom is the same as the corresponding carbon atom in the nitroso derivatives (III) and (IV),
with nitrogen oxides in a non-aqueous, aprotic system.

2. A process for preparing an N-nitroso derivative of formula (IV)

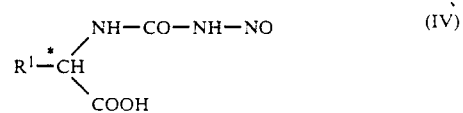

wherein
the asterisk denotes an asymmetric carbon atom having a particular stereochemical configuration, and
$R^1$ represents an optionally substituted alkyl, cycloalkyl, cycloalkenyl, aryl, or arylalkyl group,
which comprises nitrosating the corresponding N-carbamyl derivative of formula (II)

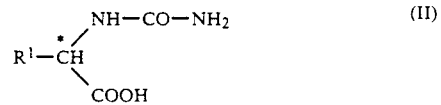

wherein
$R^1$ is as defined above and the asterisk indicates that the absolute configuration of the starred carbon atom is the same as the corresponding carbon atom in the nitroso derivative (IV),
with nitrogen oxides in a non-aqueous, aprotic system, and then submitting the thus obtained mixture of N-nitroso derivatives to acid-catalysed rearrangement.

* * * * *